(12) United States Patent
Wynn et al.

(10) Patent No.: US 8,551,449 B2
(45) Date of Patent: Oct. 8, 2013

(54) CONTRAST AGENTS

(75) Inventors: Duncan George Wynn, Amersham (GB); Ian Martin Newington, Amersham (GB); Harry John Wadsworth, Amersham (GB)

(73) Assignee: GE Healthcare AS, Oslo (NO)

( * ) Notice: Subject to any disclaimer, the term of this patent is extended or adjusted under 35 U.S.C. 154(b) by 532 days.

(21) Appl. No.: 12/739,977

(22) PCT Filed: Oct. 29, 2008

(86) PCT No.: PCT/EP2008/064632
§ 371 (c)(1),
(2), (4) Date: Apr. 27, 2010

(87) PCT Pub. No.: WO2009/056555
PCT Pub. Date: May 7, 2009

(65) Prior Publication Data
US 2010/0260685 A1 Oct. 14, 2010

(30) Foreign Application Priority Data
Oct. 30, 2007 (NO) .................................. 20075474

(51) Int. Cl.
*A61K 49/04* (2006.01)
*A61K 49/00* (2006.01)
(52) U.S. Cl.
CPC ...................................... *A61K 49/04* (2013.01)
USPC .......................................... 424/9.1; 424/9.44

(58) Field of Classification Search
USPC ........................................................ 424/9.44
See application file for complete search history.

(56) References Cited

U.S. PATENT DOCUMENTS 5,958,375 A * 9/1999 Rydeck et al. ............. 424/9.451
2004/0198834 A1 10/2004 Lasser

FOREIGN PATENT DOCUMENTS

WO WO9208691 A1 * 5/1992

OTHER PUBLICATIONS

Johnson, John "2,4,6-Triiodophenyl isocyanate as a reagent for hydroxy-and amino-groups" Journal of the Chemical Society, 1955, pp. 3322-3324.
Johnson, John "2,4,6-Triiodophenyl isocyanate as a reagent for hydroxy-and amino-groups" Chemical Abstracts Service, Columbus, Ohio, 1956.
PCT/EP2008/064632 ISRWO dated Feb. 2, 2009.

* cited by examiner

*Primary Examiner* — Michael G Hartley
*Assistant Examiner* — Melissa Perreira
(74) *Attorney, Agent, or Firm* — Yonggang Ji

(57) ABSTRACT

The present invention relates to a class of compounds and to diagnostic compositions containing such compounds where the compounds are iodine containing compounds of the formula R—Y—X—Z—R where each R denotes a triiodinated phenyl residue further substituted by hydrophilic moieties, Y and Z are urea and urethane groups and X is a alkylene group which may be further substituted. The invention also relates to the use of such diagnostic compositions as contrast agents in diagnostic imaging and in particular in X-ray imaging, and to contrast media containing such compounds.

15 Claims, No Drawings

CONTRAST AGENTS

This application is a filing under 35 U.S.C. 371 of international application number PCT/EP2008/064632, filed Oct. 29, 2008, which claims priority to Norwegian application number 20075474 filed Oct. 30, 2007, the entire disclosure of which is hereby incorporated by reference.

TECHNICAL FIELD OF THE INVENTION

The present invention relates to a class of compounds and to diagnostic compositions containing such compounds where the compounds are iodine containing compounds. More specifically the iodine containing compounds are chemical compounds containing two linked iodinated phenyl groups.

The invention also relates to the use of such diagnostic compositions as contrast agents in diagnostic imaging and in particular in X-ray imaging, and to contrast media containing such compounds.

DESCRIPTION OF RELATED ART

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedures, i.e. increased contrast can lead to increased spatial resolution.

The diagnostic quality of images is strongly dependent on the inherent noise level in the imaging procedure, and the ratio of the contrast level to the noise level can thus be seen to represent an effective diagnostic quality factor for diagnostic images.

Achieving improvement in such a diagnostic quality factor has long been and still remains an important goal. In techniques such as X-ray, magnetic resonance imaging (MRI) and ultrasound, one approach to improving the diagnostic quality factor has been to introduce contrast enhancing materials formulated as contrast media into the body region being imaged.

Thus in X-ray early examples of contrast agents were insoluble inorganic barium salts which enhanced X-ray attenuation in the body zones into which they distributed. For the last 50 years the field of X-ray contrast agents has been dominated by soluble iodine containing compounds. Commercial available contrast media containing iodinated contrast agents are usually classified as ionic monomers such as diatrizoate (marketed e.g. under the trade name Gastrografen™), ionic dimers such as ioxaglate (marketed e.g. under the trade name Hexabrix™) nonionic monomers such as iohexol (marketed e.g. under the trade name Omnipaque™), iopamidol (marketed e.g. under the trade name Isovue™), iomeprol (marketed e.g. under the trade name Iomeron™) and the non-ionic dimer iodixanol (marketed under the trade name and Visipaque™).

The most widely used commercial non-ionic X-ray contrast agents such as those mentioned above are considered safe. Contrast media containing iodinated contrast agents are used in more that 20 millions of X-ray examinations annually in the USA and the number of adverse reactions is considered acceptable. However, since a contrast enhanced X-ray examination will require up to about 200 ml contrast media administered in a total dose, there is a continuous drive to provide improved contrast media.

The utility of the contrast media is governed largely by its toxicity, by its diagnostic efficacy, by adverse effects it may have on the subject to which the contrast medium is administered, and by the ease of storage and ease of administration. Since such media are conventionally used for diagnostic purposes rather than to achieve direct therapeutic effect, it is generally desirable to provide media having as little as possible effect on the various biological mechanisms of the cells or the body as this will lead to lower toxicity and lower adverse clinical effect. The toxicity and adverse biological effects of a contrast medium are contributed to by the components of the formulation medium, e.g. the solvent or carrier as well as the contrast agent itself and its components such as ions for the ionic contrast agents and also by its metabolites.

The major contributing factors to the toxicity of the contrast medium are identified as the chemotoxicity of the contrast agent, the osmolality of the contrast medium and the ionic composition or lack thereof of the contrast medium.

Desirable characteristics of an iodinated contrast agent are low toxicity of the compound itself (chemotoxicity), low viscosity of the contrast medium wherein the compound is dissolved, low osmolality of the contrast medium and a high iodine content (frequently measured in g iodine per ml of the formulated contrast medium for administration). The iodinated contrast agent must also be completely soluble in the formulation medium, usually an aqueous medium, and remain in solution during storage.

The osmolalities of the commercial products, and in particular of the non-ionic compounds is acceptable for most media containing dimers and non-ionic monomers although there is still room for improvement. In coronary angiography for example, injection into the circulatory system of a bolus dose of contrast medium has caused severe side effects. In this procedure contrast medium rather than blood flows through the system for a short period of time, and differences in the chemical and physiochemical nature of the contrast medium and the blood that it replaces can cause undesirable adverse effects such as arrhythmias, QT prolongation and reduction in cardiac contractive force. Such effects are seen in particular with ionic contrast agents where osmotoxic effects are associated with hypertonicity of the injected contrast medium. Contrast media that are isotonic or slightly hypotonic with the body fluids are particularly desired. Low osmolar contrast media have low renal toxicity which is particularly desirable. The osmolality is a function of the number of particles per volume unit of the formulated contrast medium.

In patients with acute renal failure, nephropathy induced by contrast medium remains one of the most clinically important complications of the use of iodinated contrast medium. Aspelin, P et al, The New England Journal of Medicine, Vol. 348:491-499 (2003) concluded that nephropathy induced by contrast medium may be less likely to develop in high risk patients when iodixanol is used rather than a low-osmolar, non-ionic contrast medium.

The part of the patient population considered as high risk patients is increasing. To meet the need for continuous improvement of in vivo X-ray diagnostic agents for the entire patient population, there is a continuous drive in finding X-ray contrast agents that has improved properties, also with regards to contrast induced nephrotoxicity (CIN).

To keep the injection volume of the contrast media as low as possible it is highly desirable to formulate contrast media with high concentration of iodine/ml, and still maintain the osmolality of the media at a low level, preferably below or close to isotonicity. The development of non-ionic monomeric contrast agents and in particular non-ionic bis(tri-iodophenyl) dimers such as iodixanol (EP patent 108638) has provided contrast media with reduced osmotoxicity allowing contrast effective iodine concentration to be achieved with hypotonic solution, and has even allowed correction of ionic imbalance by inclusion of plasma ions while still maintaining the contrast medium Visipaque™ at the desired osmolality (WO 90/01194 and WO 91/13636).

The X-ray contrast media at commercial high iodine concentration have relative high viscosity, ranging from about 15 to about 60 mPas at ambient temperature. Generally, contrast media where the contrast enhancing agent is a dimer has higher viscosity than the corresponding contrast media where the contrast enhancing agent is the monomer corresponding to the dimer. Such high viscosities may pose problems to the administrators of the contrast medium, requiring relatively large bore needles or high applied pressure, and are particularly pronounced in pediatric radiography and in radiographic techniques which require rapid bolus administration, e.g. in angiography.

X-ray contrast media containing a chemical compound as the active pharmaceutical ingredient(s) having two triiodinated phenyl groups linked by a linking group are usually referred to as dimeric contrast agents or dimers. During the years a wide variety of iodinated dimers have been proposed. Relevant patent publications comprises EP 1186305, EP 686046, EP108638, EP 0049745, EP 0023992, WO 2003080554, WO2000026179, WO 1997000240, WO 9208691, U.S. Pat. No. 3,804,892, U.S. Pat. No. 4,239,747, U.S. Pat. No. 3,763,226, U.S. Pat. No. 3,763,227, U.S. Pat. No. 3,660,464 and U.S. Pat. No. 3,678,152. At this time, one contrast medium having an iodinated non-ionic dimer as the active pharmaceutical ingredient is one the market, the product Visipaque™ containing the compound iodixanol. The compound Hexabrix™, containing the ionic dimeric compound ioxaglic acid is also on the market.

Hence there still exists a desire to develop contrast agents that solves one or more of the problems discussed above. Such agents should ideally have improved properties over the soluble iodine containing compounds on the market in one or more of the following properties: renal toxicity, osmolality, viscosity, solubility, injection volumes/iodine concentration and attenuation/radiation dose and any additional adverse effect known or discovered for such iodinated compounds.

SUMMARY OF THE INVENTION

The present invention provides compounds useful as contrast media having improved properties over the known media with regards to at least one of the criteria mentioned above and in particular to renal toxicity, osmolality, viscosity and solubility. The contrast media comprises iodine containing contrast enhancing compounds where iodine containing compounds are chemical compounds containing two linked iodinated phenyl groups.

DETAILED DESCRIPTION OF THE INVENTION

The new compounds of the invention, their use as X-ray contrast agents and their formulation and production are specified in the attached claims and in the specification hereinafter.

The contrast enhancing compounds are synthetic chemical compounds of formula (I)

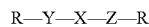   Formula (I)

and salts or optical active isomers thereof,
wherein
X denotes a $C_2$ to $C_6$ straight of branched alkylene moiety optionally interrupted by one to two oxygen atoms or sulphur atoms and wherein the alkylene moiety optionally is substituted by up to 4 —$OR^1$ groups;
Y and Z independently denote urea groups or urethane groups optionally N substituted with $C_1$ to $C_4$ straight or branched alkyl groups;
$R^1$ denotes a hydrogen atom or a $C_1$ to $C_4$ straight of branched alkyl group; and
each R independently are the same or different and denote a triiodinated phenyl group, preferably a 2,4,6-triiodinated phenyl group further substituted by two groups $R^2$ wherein each $R^2$ are the same or different and denote a hydrogen atom or a non-ionic hydrophilic moiety, provided that at least one $R^2$ group in the compound of formula (I) is a hydrophilic moiety.

In formula (I) above, X preferably denotes a straight $C_2$ to $C_6$ alkylene chain optionally substituted by one to three —$OR^1$ groups.

More preferred X denotes a straight $C_2$ to $C_5$ alkylene chain having at least one —$OR^1$ group, preferably at least one hydroxyl group in a position that is not vicinal to nitrogen atoms of the urea functions. More preferably the alkylene chain is substituted by one or two hydroxyl groups. Particular preferred groups X comprise ethylene, propylene, 2-hydroxy propylene, 2(hydroxymethyl) propylene and 2-methyl-2-hydroxy propylene. When the group X contains an asymmetric carbon atom such as e.g. the 2-hydroxy propylene moiety, then enantiomers can exist and can be separated.

$R^1$ preferably denotes a hydrogen or a methyl group, most preferred a hydrogen atom.

Y and Z are represented by urea groups of formula —N($R^3$)—CO—N($R^3$)— and urethane groups of formula —N($R^3$)—CO—O—. Preferably the nitrogen atom in the urethane group is linked to the moiety R. Z and Y may be the same, each representing urea groups or each representing urethane groups, or Z and Y may be different where one of the Z and Y entities represents a urea group, and the other of the Z and Y entities represents a urethane group.

The substituent $R^3$ denotes a hydrogen atom or a $C_1$ to $C_4$ straight of branched alkyl group. Preferably $R^3$ denotes a hydrogen atom or a methyl group. When $R^3$ denotes an alkyl group, the alkyl group is preferably bound to the nitrogen atom that is bound to the moiety X.

Hence, particularly preferred groups Y and Z are unsubstituted urea and urethane groups and the group of formula —NH—CO—N($CH_3$)—.

Each of the iodinated R groups can be the same or different and preferably denote a 2,4,6-triiodinated phenyl group, further substituted by two groups $R^2$ in the remaining 3 and 5 positions in the phenyl moiety.

The non-ionic hydrophilic moieties $R^2$ may be any of the non-ionizing groups conventionally used to enhance water solubility. Hence, the $R^2$ substituents may be the same or different and shall preferably all denote a non-ionic hydrophilic moiety comprising esters, amides and amine moieties, optionally further substituted by a straight chain or branched chain $C_{1-10}$ alkyl groups, preferably $C_{1-5}$ alkyl groups, where the alkyl groups also may have one or more $CH_2$ or $CH$ moieties replaced by oxygen or nitrogen atoms. The $R^2$ substituents may also further contain one or more groups selected from oxo, hydroxyl, amino or carboxyl derivative, and oxo substituted sulphur and phosphorus atoms. Each of the straight or branched alkyl groups preferably contains 1 to 6 hydroxy groups and more preferably 1 to 3 hydroxy groups. Therefore, in a further preferred aspect, the $R^2$ substituents are the same or different and are polyhydroxy $C_{1-5}$ alkyl, hydroxyalkoxyalkyl with 1 to 5 carbon atoms and hydroxy-polyalkoxyalkyl with 1 to 5 carbon atoms, and are attached to the iodinated phenyl group via an amide or a carbamoyl linkage, preferably amide linkages.

The $R^2$ groups of the formulas listed below are particularly preferred:

—CONH—CH$_2$—CH$_2$—OH

—CONH—CH$_2$—CHOH—CH$_2$—OH

—CON(CH$_3$)CH$_2$—CHOH—CH$_2$OH

—CONH—CH—(CH$_2$—OH)$_2$

—CON—(CH$_2$—CH$_2$—OH)$_2$

—CON—(CH$_2$—CHOH—CH$_2$—OH)$_2$

—CONH$_2$

—CONHCH$_3$

—CON(CH$_2$—CHOH—CH$_2$—OH)(CH$_2$—CH$_2$—OH)

—CONH—C(CH$_2$OH)$_3$

—CONH—CH(CH$_2$—OH)(CHOH—CH$_2$—OH)

—CONH—CH(CH$_2$—OH)(CHOH—CH$_2$—OH), and

-morpholine-4-carbonyl.

Even more preferably the $R^2$ groups will be equal or different and denote amide group compounds, preferably one or more moieties of the formulas —CONH—CH$_2$—CHOH—CH$_2$—OH, —CON(CH$_3$)CH$_2$—CHOH—CH$_2$OH, —CONH—CH—(CH$_2$—OH)$_2$, —CON—(CH$_2$—CH$_2$OH)$_2$ and —CON—(CH$_2$—CHOH—CH$_2$—OH)$_2$. Still more preferably both R groups are the same and the $R^2$ groups in each R are the same or different and denote —CONH—CH$_2$—CHOH—CH$_2$—OH and —CON—(CH$_2$—CH$_2$OH—CH$_2$OH)$_2$. Most preferred all substituents $R^2$ are the same.

Thus, preferred structures according to the invention include the compounds of formula (II):

Formula (II)

R—NH—CO—N(R$^3$)—X—N(R$^3$)—CO—NH—R  (IIa)

R—NH—CO—O—X—O—CO—NH—R  (IIb)

R—NH—CO—O—X—N(R$^3$)—CO—NH—R  (IIc)

In formulas (II), each group R has the meaning above, more preferably each iodophenyl groups R are the same and the $R^2$ groups all denote non-ionic hydrophilic moieties, and preferably the $R^2$ groups are linked to iodinated phenyl moiety by amide linkages. $R^3$ and X has the meanings above and X preferably denotes straight chain alkylene groups with 2 to 5 carbon atoms and straight or branched mono-hydroxylated alkylene groups where the hydroxyl substituent are at positions that are not adjacent to the nitrogen function.

Preferred examples the structures according to the invention include the compounds of formulas (III a) to (III n) below.

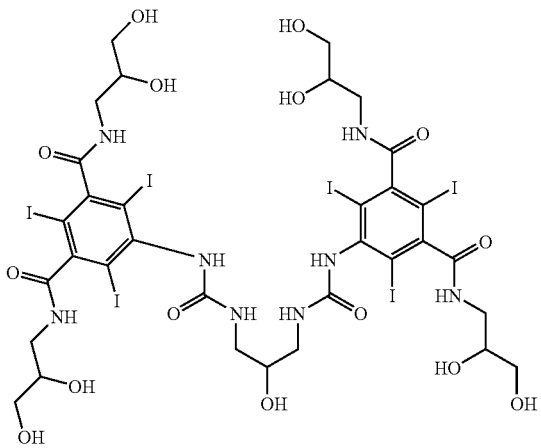

Formula IIIa

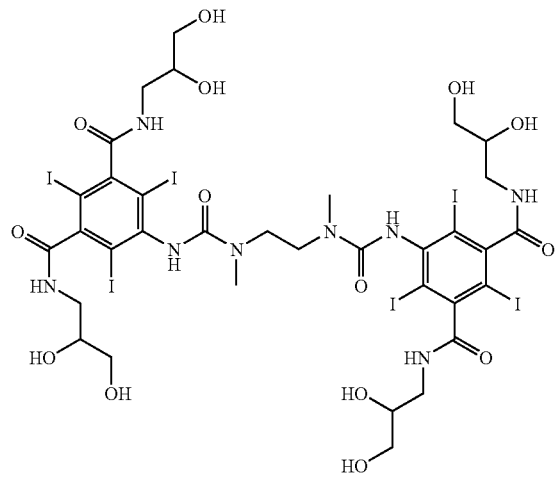

Formula IIIb

-continued
Formula IIIc
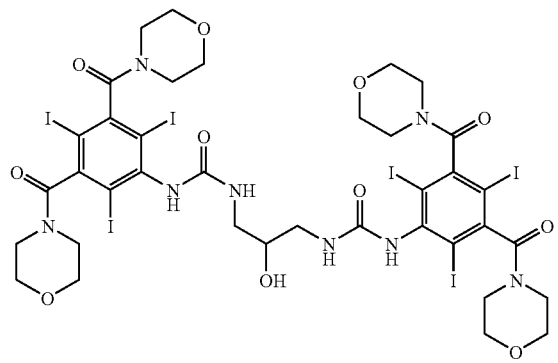
Formula IIId
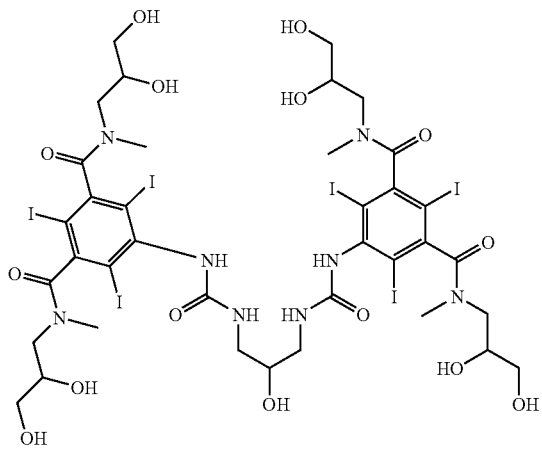
Formula IIIe
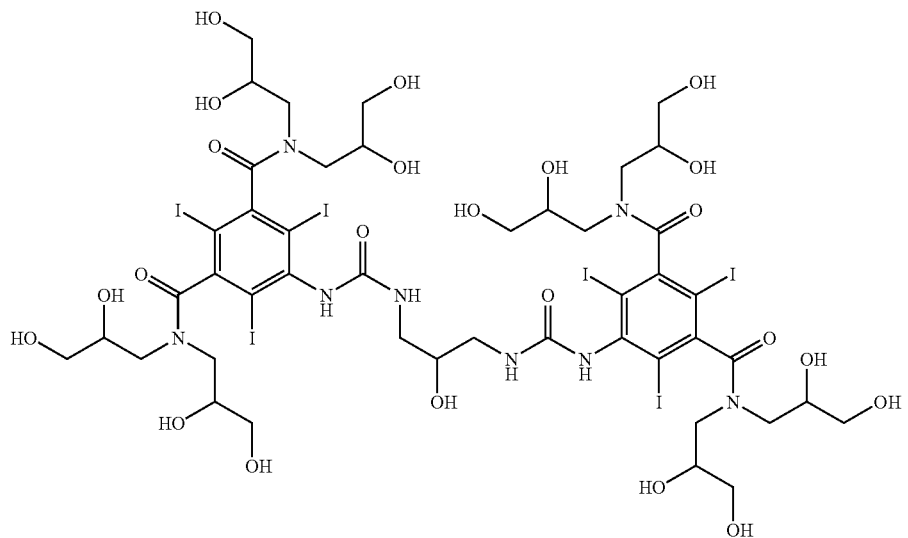
Formula IIIf
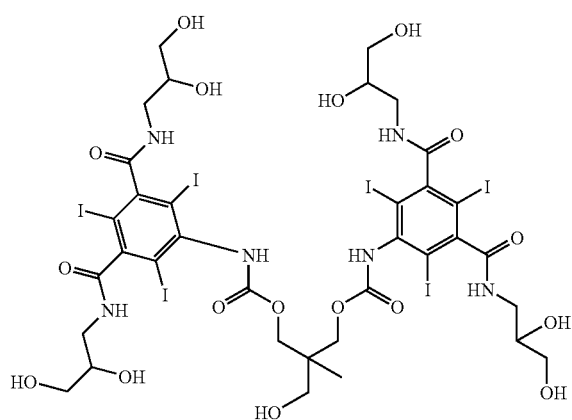

Formula IIIg
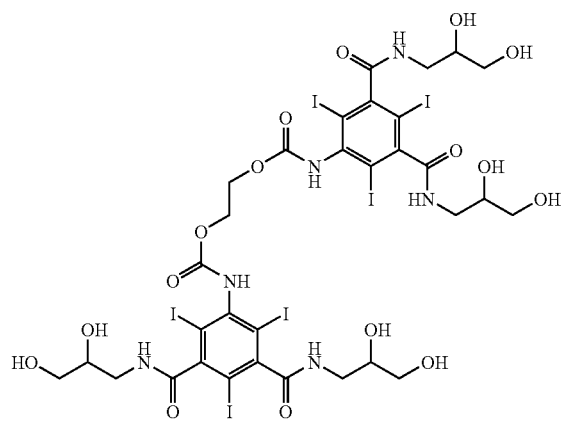
Formula IIIh
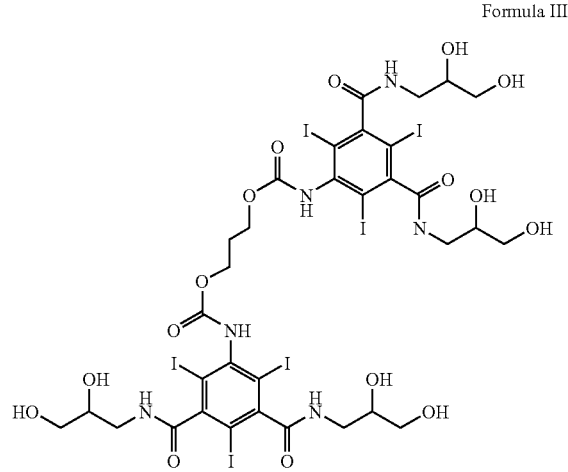
Formula IIIi
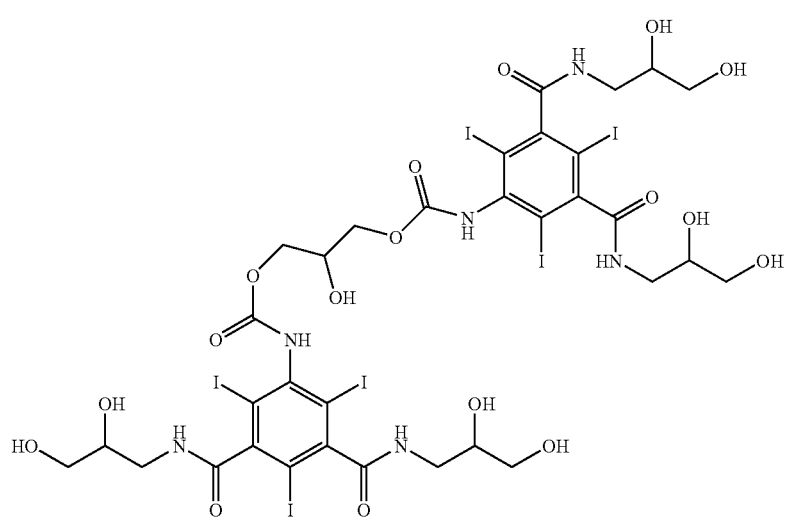
Formula IIIj
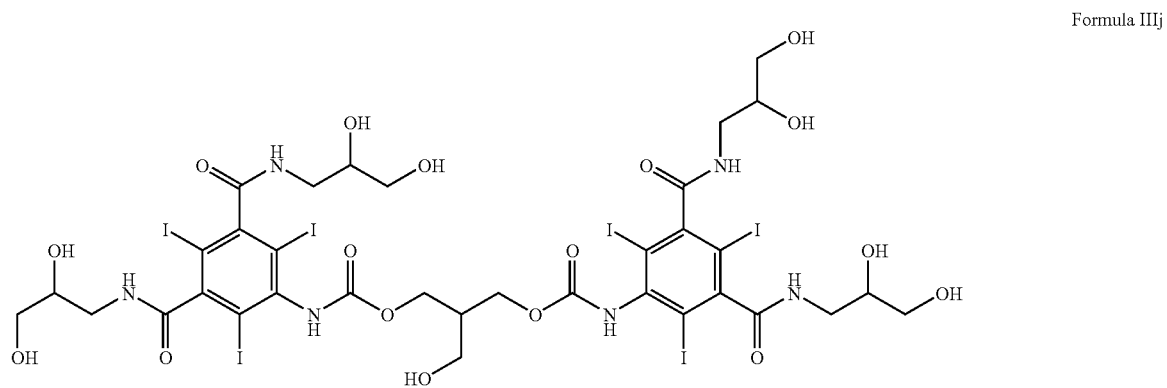

Formula IIIk
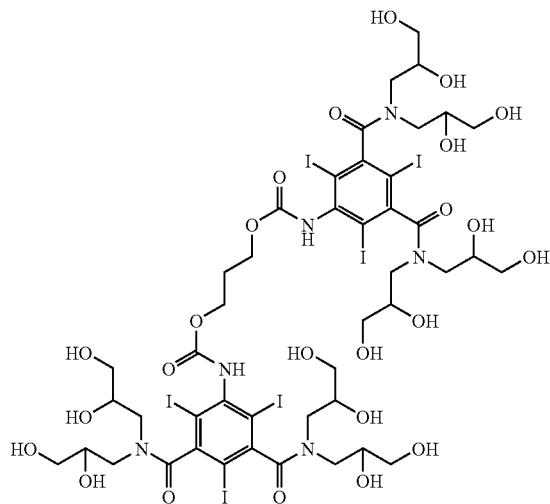
Formula IIIl
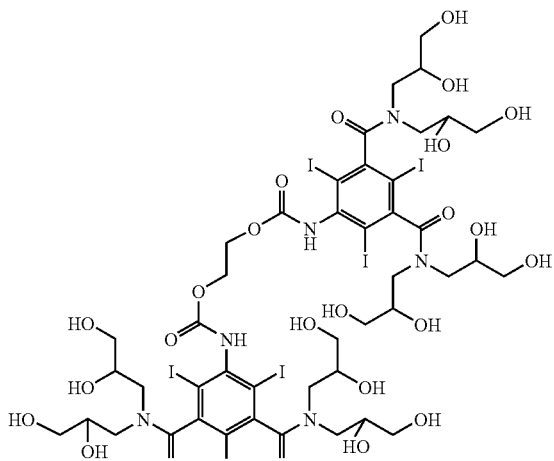
Formula IIIm
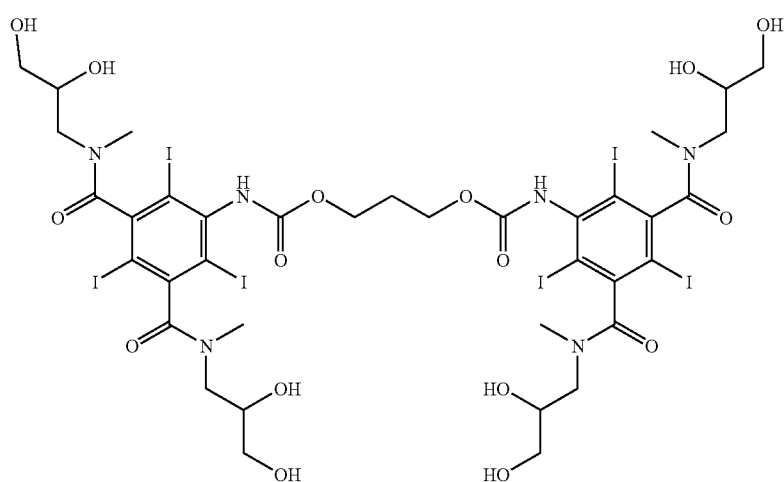
Formula IIIn
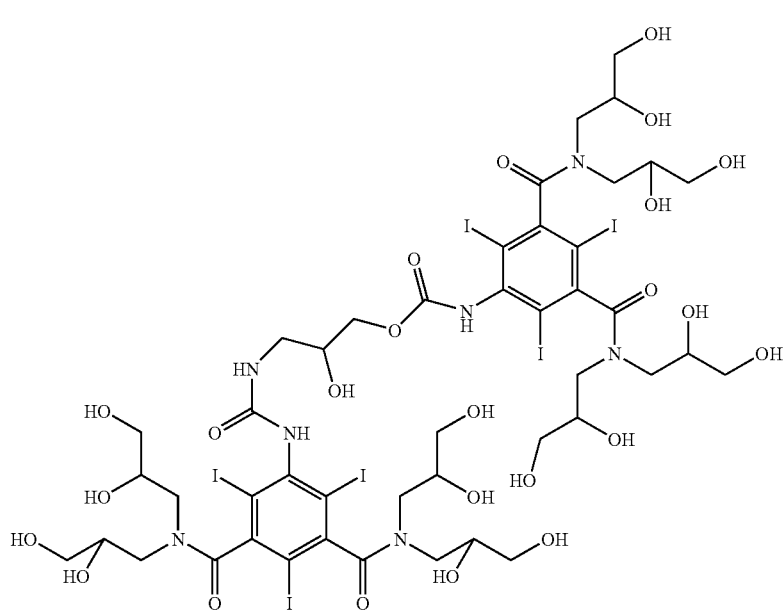

At an iodine concentration of 320 mg/ml, which is a common concentration for commercially available iodinated contrast media, the concentration of the compound of formula (I) will be approximately 0.42 M (Molar). The contrast medium will also be hypoosmolar at this iodine concentration, and this is an advantageous property with regards to the nephrotoxicity of the contrast medium. It is also possible to add electrolytes to the contrast medium to lower the cardiovascular effects as explained in WO 90/01194 and WO 91/13636.

Compounds of formula (I) also comprises optical active isomers and may exist in several isomeric forms due to chiral carbon atoms. Both enantiomerically pure products as well as mixtures of optical isomers are included.

The compounds of the invention may be used as contrast agents and may be formulated with conventional carriers and excipients to produce diagnostic contrast media.

Thus viewed from a further aspect the invention provides a diagnostic composition comprising a compound of formula (I) as described above together with at least one physiologically tolerable carrier or excipient, e.g. in aqueous solution for injection optionally together with added plasma ions or dissolved oxygen.

The contrast agent composition of the invention may be in a ready to use concentration or may be a concentrate form for dilution prior to administration. Generally compositions in a ready to use form will have iodine concentrations of at least 100 mg I/ml, preferably at least 150 mg I/ml, with concentrations of at least 300 mg I/ml, e.g. 320 mg I/ml being preferred. The higher the iodine concentration, the higher is the diagnostic value in the form of X-ray attenuation of the contrast media. However, the higher the iodine concentration the higher is the viscosity and the osmolality of the composition. Normally the maximum iodine concentration for a given contrast media will be determined by the solubility of the contrast enhancing agent, e.g. the iodinated compound, and the tolerable limits for viscosity and osmolality.

For contrast media which are administered by injection or infusion, the desired upper limit for the solution's viscosity at ambient temperature (20° C.) is about 30 mPas, however viscosities of up to 50 to 60 mPas and even more than 60 mPas can be tolerated. For contrast media given by bolus injection, e.g. in angiographic procedures, osmotoxic effects must be considered and preferably the osmolality should be below 1 Osm/kg $H_2O$, preferably below 850 mOsm/kg $H_2O$ and more preferably about 300 mOsm/kg $H_2O$.

With the compounds of the invention such viscosity, osmolality and iodine concentrations targets can be met. Indeed, effective iodine concentrations can be reached with hypotonic solutions. It may thus be desirable to make up the solution's tonicity by the addition of plasma cations so as to reduce the toxicity contribution that derives from the imbalance effects following bolus injection. Such cations will desirably be included in the ranges suggested in WO 90/01194 and WO 91/13636.

In particular, addition of sodium and calcium ions to provide a contrast medium isotonic with blood for all iodine concentrations is desirable and obtainable. The plasma cations may be provided in the form of salts with physiologically tolerable counterions, e.g. chloride, sulphate, phosphate, hydrogen carbonate etc., with plasma anions preferably being used.

The contrast media containing compounds of formula (I) can be administered by injection or infusion, e.g. by intravascular administration. Alternatively, contrast media containing compounds of formula (I) may also be administered orally. For oral administration the contrast medium may be in the form of a capsule, tablet or as liquid solution.

In a further embodiment the invention provides diagnostic agents comprising a compound of formula (I) and diagnostic compositions comprising a compound of formula (I) together with pharmaceutically acceptable carriers or excipients. The diagnostic agents and composition are preferably for use in X-ray diagnosis.

Hence, the invention further embraces use of a diagnostic agent and a diagnostic composition containing a compound of formula (I) in X-ray contrast examinations and use of a compound of formula (I) for the manufacture of a diagnostic composition for use as an X-ray contrast agent.

A method of diagnosis comprising administration of compounds of formula (I) to the human or animal body, examining the body with a diagnostic device and compiling data from the examination is also provided. In the method of diagnosis the body may also be preadministrated with compounds of formula (I).

Furthermore, a method of imaging, specifically X-ray imaging is provided, which comprises administration of compounds of formula (I) to the human or animal body, examining the body with a diagnostic device and compiling data from the examination and optionally analysing the data. In the method of imaging the body may also be preadministrated with compounds of formula (I).

Preparation

The compounds of the general formula (I) can be synthesized by multistep procedures from starting materials that are either known from the state of art or that are commercially available or can readily be producted from commercially available materials.

General procedure for preparation of compounds of formula (I) is illustrated in Examples 1 to 14.

In general, compounds of formula (IIa), (IIb) and (IIc) (collectively denotes formula (II))

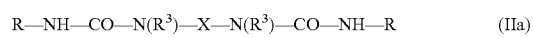
R—NH—CO—N(R³)—X—N(R³)—CO—NH—R    (IIa)

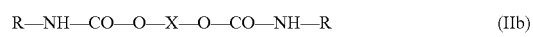
R—NH—CO—O—X—O—CO—NH—R    (IIb)

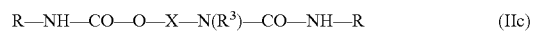
R—NH—CO—O—X—N(R³)—CO—NH—R    (IIc)

can be prepared by reacting a compound of formula (IV)

R'-A    (IV)

with a compound of formula (V)

B—X'—B    (V)

wherein R' denotes R or a precursor or protected derivative thereof;

X' denotes X or a precursor or protected derivative thereof;

A denotes an isocyanate residue: and each B are the same or different denotes a primary amine, secondary amine or an alcohol.

A solution of compound of formula (IV) is added to a solution of 0.5 equivalents of a compound of formula (V) in dichloromethane. The mixture is stirred at 25° C. for 18 h when analysis indicates complete reaction. Solvent is removed under vacuum and the product is isolated by chromatography on silica gel.

The final compounds of formula (II) are prepared from these products by dihydroxylation or by removal of protecting groups as appropriate.

Preparation of Intermediates:

All the alkylene diamines and alkylene diols are available from commercial suppliers.

Preparation of acetic acid 1-acetoxymethyl-2-[3-(2,3-diacetoxy-propylcarbamoyl)-2,4,6-triiodo-5-isocyanato-benzoylamino]-ethyl ester

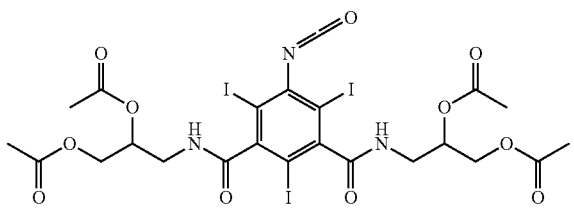

To a solution of acetic acid 1-acetoxymethyl-2-[3-amino-5-(2,3-diacetoxy-propylcarbamoyl)-2,4,6-triiodo-benzoylamino]-ethyl ester (15 g, 17 mmol) in 1,4-dioxane (40 mL) was added a solution of 20% phosgene in toluene (100 mL, 11 eq) at ambient temperature. The mixture was then heated to 60° C. for 15 hours. The reaction mixture was cooled to ambient temperature and then concentrated at reduced pressure to give an off white solid. Dioxane (50 mL×2) was added and removed slowly at reduced pressure to give an off-white solid which was placed on a vacuum line to remove any residual solvent. The material was used without further purification $^1$H NMR (CDI$_3$): 7.02 (s, br, 2H), 5.29-5.21 (m, 2H), 4.50-4.38 (m, 2H), 4.30-4.19 (m, 2H), 3.82-3.48 (m, 4H), 2.05 (s, 12H)

$^{13}$C NMR (CDCl3): 170.7, 170.3, 169.7, 149.8, 123.7, 92.2, 70.0, 63.3, 39.9, 21.3, 20.7

Using the same procedure, the following isocyanates were prepared:

N,N,N',N'-Tetraallyl-2,4,6-triiodo-5-isocyanato-isophthalamide

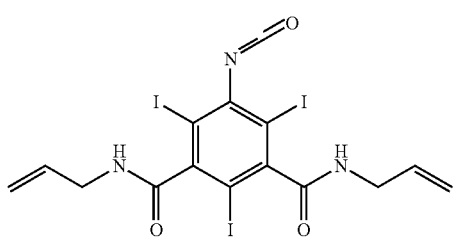

$^1$H NMR (CDCl$_3$): 5.91-5.84 (m, 4H), 5.38-4.91 (m, 8H), 4.28-4.02 (m, 4H), 3.68 (d, 4H, J=6 Hz)

N,N'-Diallyl-2,4,6-triiodo-5-isocyanato-N,N'-dimethyl-isophthalamide

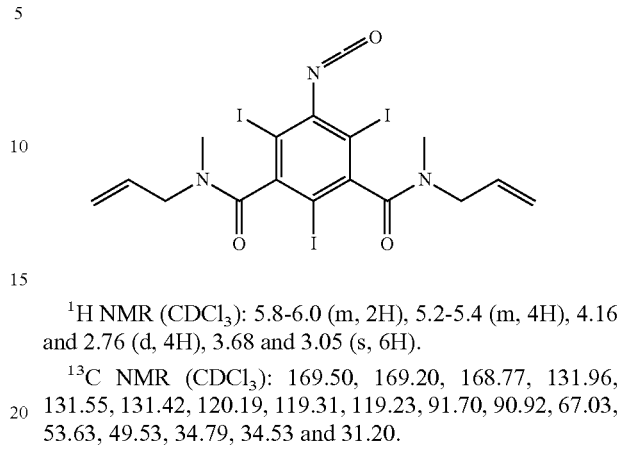

$^1$H NMR (CDCl$_3$): 5.8-6.0 (m, 2H), 5.2-5.4 (m, 4H), 4.16 and 2.76 (d, 4H), 3.68 and 3.05 (s, 6H).

$^{13}$C NMR (CDCl$_3$): 169.50, 169.20, 168.77, 131.96, 131.55, 131.42, 120.19, 119.31, 119.23, 91.70, 90.92, 67.03, 53.63, 49.53, 34.79, 34.53 and 31.20.

N,N'-Diallyl-2,4,6-triiodo-5-isocyanatoisophthalamide

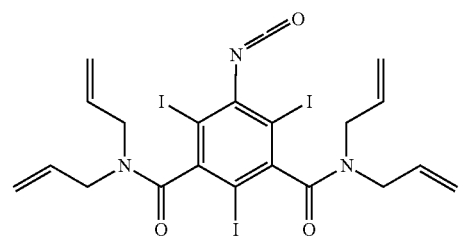

$^1$H NMR (d6DMSO): 8.61 (t, NH), 5.81-5.96 (m, 2H), 3.30-4.05 (complex 8H)

$^{13}$C NMR (d6DMSO): 170.20, 149.52, 147.99, 135.23, 116.60, 107.15, 80.60, 53.04, 45.64, 42.07, 36.24, 8.93, and 7.86.

1,3-Bis(4-morpholinocarbonyl)-2,4,6-triiodo-5-isocyanotobenzene

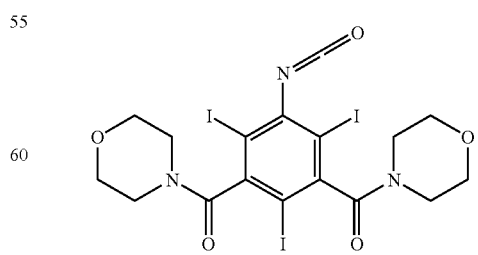

$^1$H NMR (CDCl$_3$): 3.67-3.80 (m, 6H) and 3.16-3.23 (m, 2H).

$^{13}$C NMR (CDCl$_3$): 168.78, 168.05, 149.09, 147.64, 141.09, 123.64, 91.67, 84.41, 66.92, 66.18, 65.90, 46.26 and 41.58.

EXPERIMENTAL

Example 1

1,3-bis-[N,N'-Bis-(2,3-dihydroxy-propyl)-2,4,6-triiodo-5-ureido-isophthalamide]-2-hydroxypropane

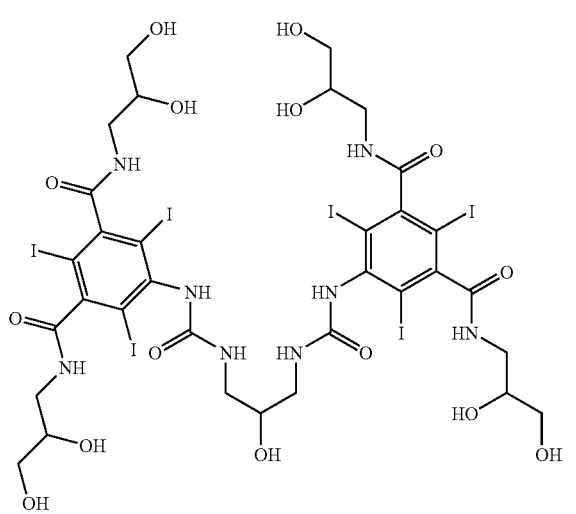 [SMILES: O=C(NCC(O)CNC(=O)Nc1c(I)c(C(=O)NCC(O)CO)c(I)c(C(=O)NCC(O)CO)c1I)Nc1c(I)c(C(=O)NCC(O)CO)c(I)c(C(=O)NCC(O)CO)c1I]

To a solution of acetic acid 1-acetoxymethyl-2-[3-(2,3-diacetoxy-propylcarbamoyl)-2,4,6-triiodo-5-isocyanato-benzoylamino]-ethyl ester in dichloromethane was added 1,3-diamino-2-hydroxypropane (0.5 equivalent). The reaction mixture was stirred for 18 hours and then purified by column chromatography to give Acetic acid 2-acetoxy-3-[3-[3-(3-{3-[3,5-bis-(2,3-diacetoxy-propylcarbamoyl)-2,4,6-triiodo phenyl]-ureido}-2-hydroxy-propyl)-ureido]-5-(2,3-diacetoxy-propylcarbamoyl)-2,4,6-triiodo-benzoylamino]-propyl ester. This was dissolved in methanol and treated with aqueous ammonia. The material was purified by preparatie HPLC to give 1,3-bis-[N,N'-Bis-(2,3-dihydroxy-propyl)-2,4,6-triiodo-5-ureido-isophthalamide]-2-hydroxypropane as a white powder after freeze drying.

MS (ES$^+$, m/z): 1552.89 (100%)

Example 2

1,3-bis-[N,N'-Bis-(2,3-dihydroxy-propyl)-2,4,6-triiodo-5-(methyl-ureido)-isophthalamide]-ethylene

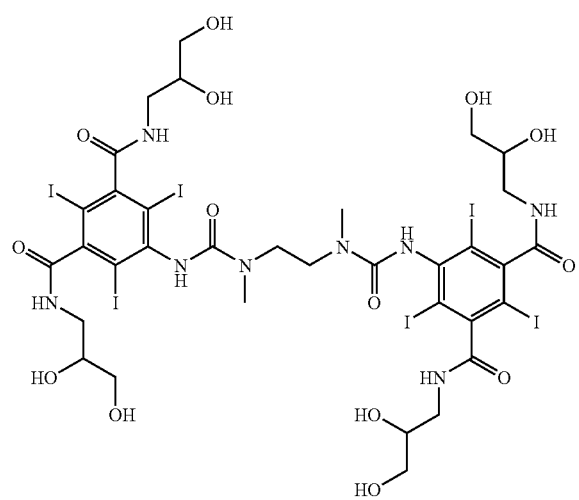 [SMILES: CN(CCN(C)C(=O)Nc1c(I)c(C(=O)NCC(O)CO)c(I)c(C(=O)NCC(O)CO)c1I)C(=O)Nc1c(I)c(C(=O)NCC(O)CO)c(I)c(C(=O)NCC(O)CO)c1I]

To a solution of acetic acid 1-acetoxymethyl-2-[3-(2,3-diacetoxy-propylcarbamoyl)-2,4,6-triiodo-5-isocyanato-benzoylamino]-ethyl ester in dichloromethane was added N,N'-dimethylethylenediamine (0.5 equivalent). The reaction mixture was stirred for 18 hours and then purified by column chromatography to give acetic acid 2-acetoxy-3-[3-[3-(2-{3-[3,5-bis-(2,3-diacetoxy-propylcarbamoyl)-2,4,6-triiodo-phenyl]-1-methyl-ureido}ethyl)-3-methyl-ureido]-5-(2,3-diacetoxy-propylcarbamoyl)-2,4,6-triiodo-benzoylamino]-propyl ester. This was dissolved in methanol and treated with aqueous ammonia. The material was purified by preparative HPLC to give 1,3-bis-[N,N'-Bis-(2,3-dihydroxy-propyl)-2,4, 6-triiodo-5-(methyl-ureido)-isophthalamide]-ethylene as a white powder after freeze drying.

MS (ES$^+$, m/z): ES(+) 804.01; 1552.51

Example 3

1,3-bis-[N,N'-Bis-(4-morpholine)-2,4,6-triiodo-5-ureido-isophthalamide]-2-hydroxypropane

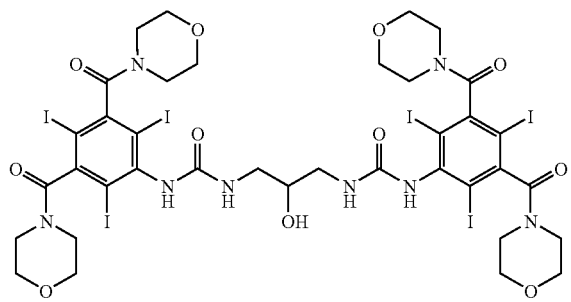 [SMILES: O=C(NCC(O)CNC(=O)Nc1c(I)c(C(=O)N2CCOCC2)c(I)c(C(=O)N2CCOCC2)c1I)Nc1c(I)c(C(=O)N2CCOCC2)c(I)c(C(=O)N2CCOCC2)c1I]

To a solution of 1,3-Bis(4-morpholinocarbonyl)-2,4,6-triiodo-5-isocyanotobenzene in dichloromethane was added 1,3-diamino-2-hydroxypropane (0.5 equivalent). The reaction mixture was stirred for 18 hours and then purified by column chromatography to give 1,3-bis-[N,N'-Bis-(4-morpholine)-2,4,6-triiodo-5-ureido-isophthalamide]-2-hydroxypropane. This was treated to preparative HPLC and freeze dried to give a white powder.

MS (ES$^-$, m/z): 1535.46 (100%)

Example 4

1,3-Bis-[bis-N,N'-methyl-N,N'-bis-(2,3-dihydroxy-propyl)-2,4,6-triiodo-5-ureido-isophthalamide]-2-hydroxypropane To a solution of N,N'-Diallyl-2,4,6-triiodo-5-isocyanato-N,N'-dimethyl-isophthalamide in dichloromethane was added 1,3-diamino-2-hydroxypropane (0.5 equivalent). The reaction mixture was stirred for 18 hours and then purified by column chromatography to give 1,3-Bis-[bis-N,N'-methyl-N,N'-bis-(allyl)-2,4,6-triiodo-5-ureido-isophthalamide]-2-hydroxypropane. A cis-dihydroxylation using OsO$_4$ and NMMO was performed and the crude mixture was purified by preparative HPLC to give 1,3-Bis-[bis-N,N'-methyl-N,N'-bis-(2,3-dihydroxy-propyl)-2,4,6-triiodo-5-ureido-isophthalamide]-2-hydroxypropane as a white powder after freeze drying.

MS (ES$^+$, m/z): 1608.77 (100%)

Example 5

1,3-bis-(N,N,N',N'-tetrakis-(2,3-dihydroxypropyl))-2,4,6-triiodo-5-ureido-isophthalamide]-2-hydroxypropane

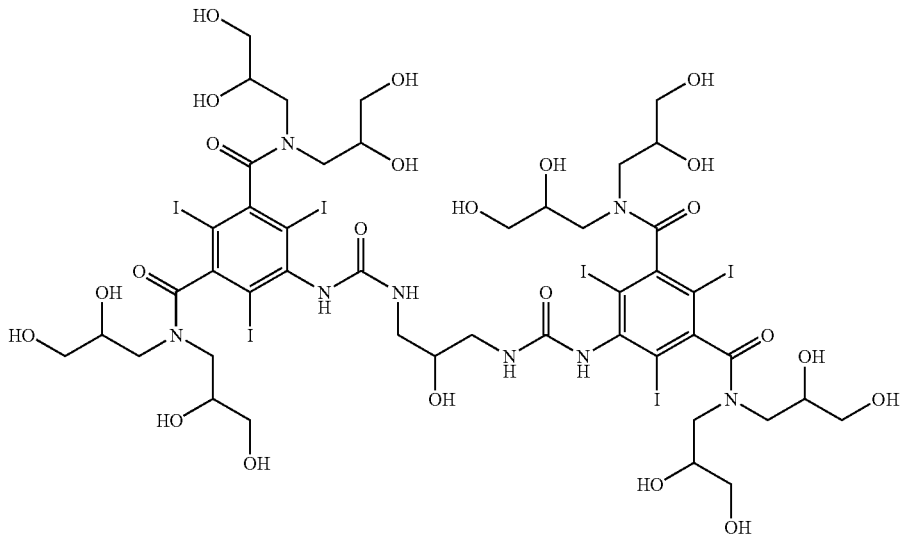 [SMILES: O=C(NCC(O)CNC(=O)Nc1c(I)c(C(=O)N(CC(O)CO)CC(O)CO)c(I)c(C(=O)N(CC(O)CO)CC(O)CO)c1I)Nc1c(I)c(C(=O)N(CC(O)CO)CC(O)CO)c(I)c(C(=O)N(CC(O)CO)CC(O)CO)c1I]

To a solution of N,N'-Diallyl-2,4,6-triiodo-5-isocyanatoisophthalamide in dichloromethane was added 1,3-diamino-2-hydroxypropane (0.5 equivalent). The reaction mixture was stirred for 18 hours and then purified by column chromatography to give 1,3-Bis-[N,N'-bis-(diallyl)-2,4,6-triiodo-5-ureido-isophthalamide]-2-hydroxypropane. A cis-dihydroxylation using $OsO_4$ and NMMO was performed and the crude mixture was purified by preparative HPLC to give 1,3-bis-(N,N,N',N'-tetrakis-(2,3-dihydroxypropyl))-2,4,6-triiodo-5-ureido-isophthalamide]-2-hydroxypropane as a white powder after freeze drying.

MS ($ES^+$, m/z): 1848.63 (100%)

Example 6

1,3-bis-[N,N'-Bis-(2,3-dihydroxy-propyl)-2,4,6-triiodo-5-carbamido-isophthalamide]-2-methyl-2-hydroxymethylpropane

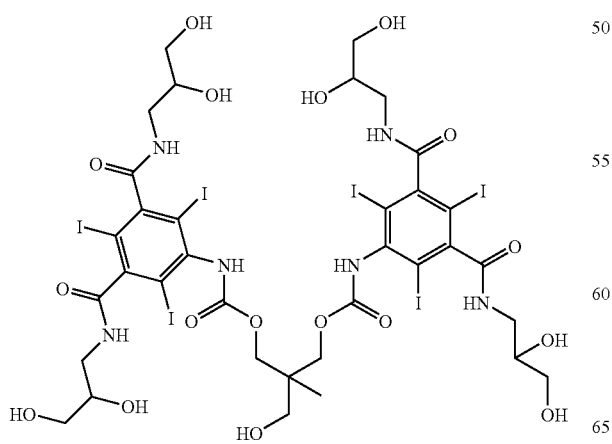

To a solution of acetic acid 1-acetoxymethyl-2-[3-(2,3-diacetoxy-propylcarbamoyl)-2,4,6-triiodo-5-isocyanato-benzoylamino]-ethyl ester in dichloromethane was added 1,1,1-tris(hydroxymethyl)ethane (0.3 equivalent). The reaction mixture was stirred for 18 hours and then purified by column chromatography to give acetic acid 2-acetoxy-3-[3-{2-[3,5-bis-(2,3-diacetoxy-propylcarbamoyl)-2,4,6-triiodo-phenylcarbamoyloxymethyl]-3-hydroxy-2-methyl-propoxycarbonylamino}-5-(2,3-diacetoxy-propylcarbamoyl)-2,4,6-triiodo-benzoylamino]propyl ester. This was dissolved in methanol and treated with aqueous ammonia. The material was purified by preparatie HPLC to give 1,3-bis-[N,N'-Bis-(2,3-dihydroxy-propyl)-2,4,6-triiodo-5-carbamido-isophthalamide]-2-methyl-2-hydroxymethylpropane as a white powder after freeze drying.

MS ($ES^+$, m/z): 1582.79 (100%)

Example 7

{3,5-Bis-[bis-(2,3-dihydroxy-propyl)-carbamoyl]-2,4,6-triiodo-phenyl}-carbamic acid 2-{3,5-bis-[bis-(2,3-dihydroxy-Propyl)-carbamoyl]-2,4,6-triiodo-phenylcarbamoyloxy}-ethyl ester

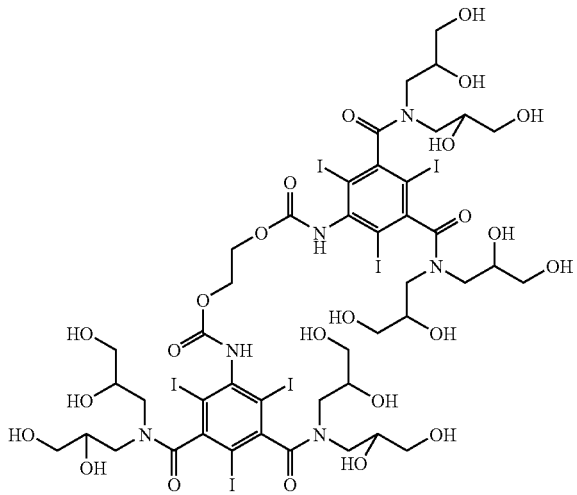 [SMILES: O=C(Nc1c(I)c(C(=O)N(CC(O)CO)CC(O)CO)c(I)c(C(=O)N(CC(O)CO)CC(O)CO)c1I)OCCOC(=O)Nc1c(I)c(C(=O)N(CC(O)CO)CC(O)CO)c(I)c(C(=O)N(CC(O)CO)CC(O)CO)c1I]

To a solution of N,N'-Di-allyl-2,4,6-triiodo-5-isocyanatoisophthalamide in dichloromethane was added ethylene glycol (0.5 equivalent). The reaction mixture was stirred for 18 hours and then purified by column chromatography to give (3,5-Bis-diallylcarbamoyl-2,4,6-triiodo-phenyl)-carbamic acid 2-(3,5-bis-diallylcarbamoyl-2,4,6-triiodo-phenylcarbamoyloxy)-ethyl ester. A cis-dihydroxylation using $OsO_4$ and NMMO was performed and the crude mixture was purified by preparative HPLC to give 1,3-bis-(N,N,N',N'-tetrakis-(2,3-dihydroxypropyl))-2,4,6-triiodo-5-ureido-isophthalamide]-2-hydroxypropane as a white powder after freeze drying.

MS ($ES^+$, m/z): 1821.39 (100%)

Example 8

{3,5-Bis-[bis-(2,3-dihydroxy-propyl)-carbamoyl]-2,4,6-triiodo-phenyl}-carbamic acid 3,5-bis-{3-[bis-(2,3-dihydroxy-propyl)-carbamoyl]-2,4,6-triiodo-phenylcarbamoyloxy}-propyl ester

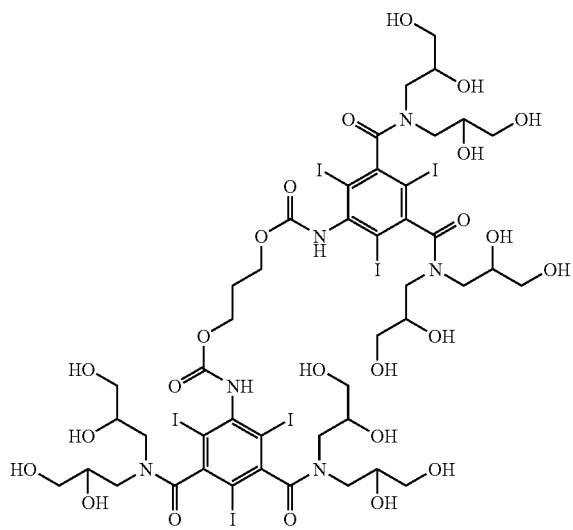 [SMILES: O=C(Nc1c(I)c(C(=O)N(CC(O)CO)CC(O)CO)c(I)c(C(=O)N(CC(O)CO)CC(O)CO)c1I)OCCCOC(=O)Nc1c(I)c(C(=O)N(CC(O)CO)CC(O)CO)c(I)c(C(=O)N(CC(O)CO)CC(O)CO)c1I]

This compound is prepared following this procedure of Example 7.

MS ($ES^+$, m/z): 1835.46 (100%)

Example 9

[3,5-Bis-(2,3-dihydroxy-propylcarbamoyl)-2,4,6-triiodo-phenyl]-carbamic acid 2-[3,5-bis-(2,3-dihydroxy-propylcarbamoyl)-2,4,6-triiodo-phenylcarbamoyloxy]-ethyl ester

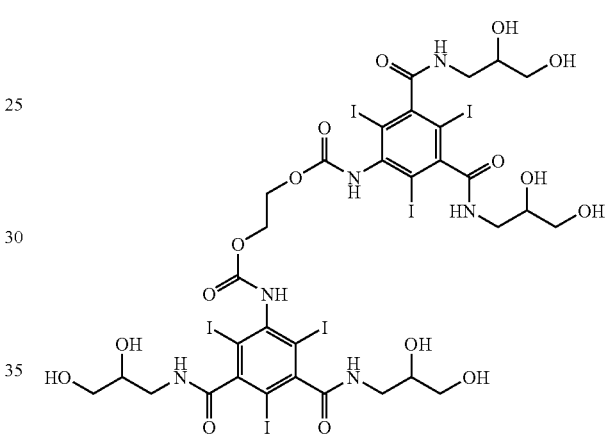

To a solution of acetic acid 1-acetoxymethyl-2-[3-(2,3-diacetoxy-propylcarbamoyl)-2,4,6-triiodo-5-isocyanatobenzoylamino]-ethyl ester in dichloromethane was added ethylene glycol (0.5 equivalent). The reaction mixture was stirred for 18 hours and then purified by column chromatography to give acetic acid 2-acetoxy-3-(3,5-bis-{2-[3,5-bis-(2,3-diacetoxy-propylcarbamoyl)-2,4,6-triiodo-phenylcarbamoyloxy]-ethoxycarbonylamino}-2,4,6-triiodo-benzoylamino)-propyl ester. This was dissolved in methanol and treated with aquesous ammonia. The material was purified by preparative HPLC to give [3,5-Bis-(2,3-dihydroxy-propylcarbamoyl)-2,4,6-triiodo-phenyl]-carbamic acid 2-[3,5-bis-(2,3-dihydroxy-propylcarbamoyl)-2,4,6-triiodo-phenylcarbamoyloxy]-ethyl ester as a white powder after freeze drying.

MS ($ES^+$, m/z): 1524.08 (100%)

Example 10

[3,5-Bis-(2,3-dihydroxy-propylcarbamoyl)-2,4,6-triiodo-phenyl]-carbamic acid 3-[3,5-Bis-(2,3-dihydroxy-Propylcarbamoyl)-2,4,6-triiodo-phenylcarbamoyloxy]-propyl ester

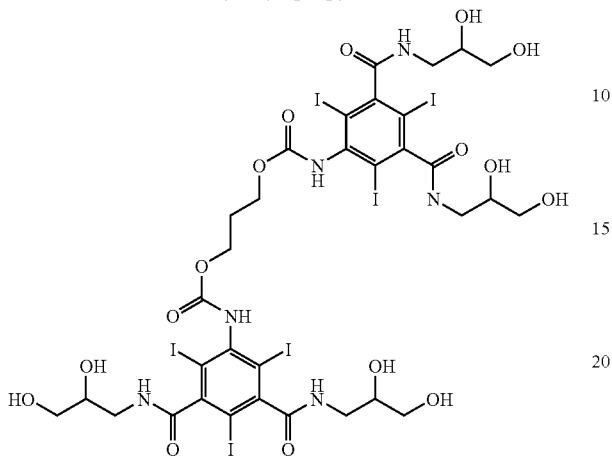

This compound is prepared following this procedure of Example 9.

MS (ES$^+$, m/z): 1540.30 (100%)

Example 11

[3,5-Bis-(2,3-dihydroxy-propylcarbamoyl)-2,4,6-triiodo-phenyl]-carbamic acid 3-[3,5-Bis-(2,3-dihydroxy-propylcarbamoyl)-2,4,6-triiodo-phenylcarbamoyloxy]-2-hydroxypropyl ester

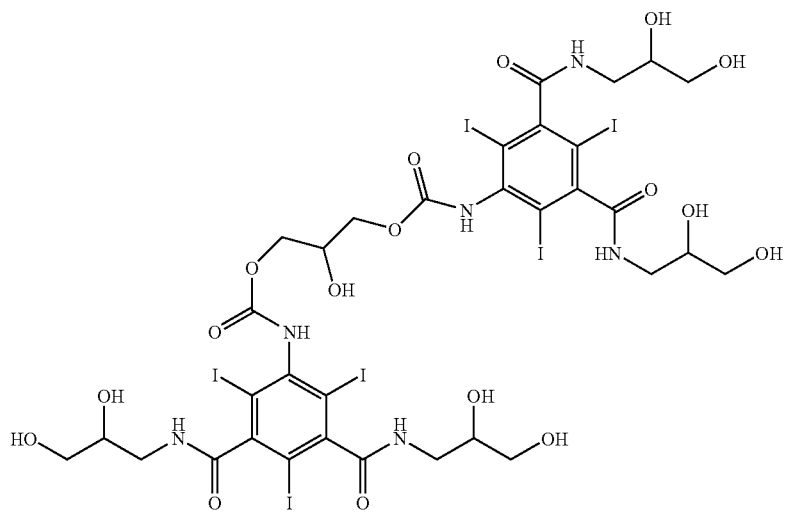 [SMILES: O=C(Nc1c(I)c(C(=O)NCC(O)CO)c(I)c(C(=O)NCC(O)CO)c1I)OCC(O)COC(=O)Nc1c(I)c(C(=O)NCC(O)CO)c(I)c(C(=O)NCC(O)CO)c1I]

This compound is prepared following this procedure of Example 9.

MS (ES$^+$, m/z): 1556.37 (65%), 797.90 (100%)

Example 12

[3,5-Bis-(2,3-dihydroxy-propylcarbamoyl)-2,4,6-triiodo-phenyl]-carbamic acid 3-[3,5-Bis-(2,3-dihydroxy-propylcarbamoyl)-2,4,6-triiodo-phenylcarbamoyloxy]-2-hydroxymethyl-propyl ester The compound was prepared following the procedure of Example 7.

cis-dihydroxylation using OsO$_4$ and NMMO was performed and the crude mixture was purified by preparative HPLC to give {3,5-Bis-[bis-(2,3-dihydroxy-propyl)-carbamoyl]-2,4,6-triiodo-phenyl}-carbamic acid 3-{3,5-Bis-[bis-(2,3-dihydroxy-propyl)-carbamoyl]-2,4,6-triiodo-phenylcarbamoyloxy}propyl ester as a white powder after freeze drying.

MS (ES$^+$, m/z): 1594.47 (100%)

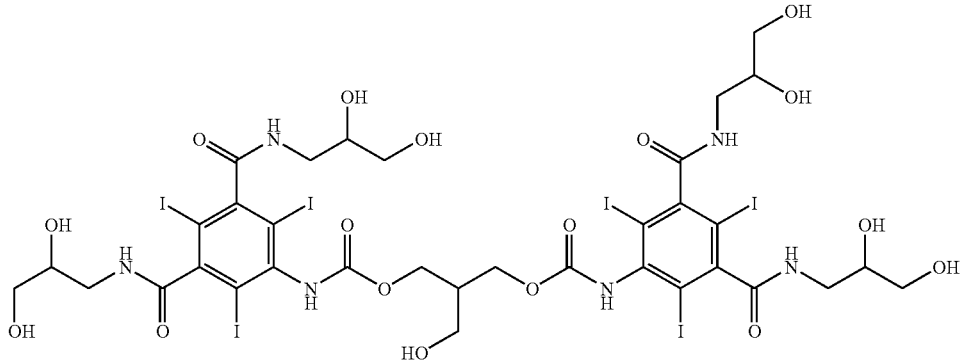 [SMILES: O=C(Nc1c(I)c(C(=O)NCC(O)CO)c(I)c(C(=O)NCC(O)CO)c1I)OCC(CO)COC(=O)Nc1c(I)c(C(=O)NCC(O)CO)c(I)c(C(=O)NCC(O)CO)c1I]

MS (ES$^+$, m/z): 1569.92 (95%), 749.07 (100%)

Example 13

{3,5-Bis-[bis-(2,3-dihydroxy-propyl)-carbamoyl]-2,4,6-triiodo-phenyl}-carbamic acid 3-{3,5-Bis-[bis-(2,3-dihydroxy-propyl)-carbamoyl]-2,4,6-triiodo-phenylcarbamoyloxy}propyl ester

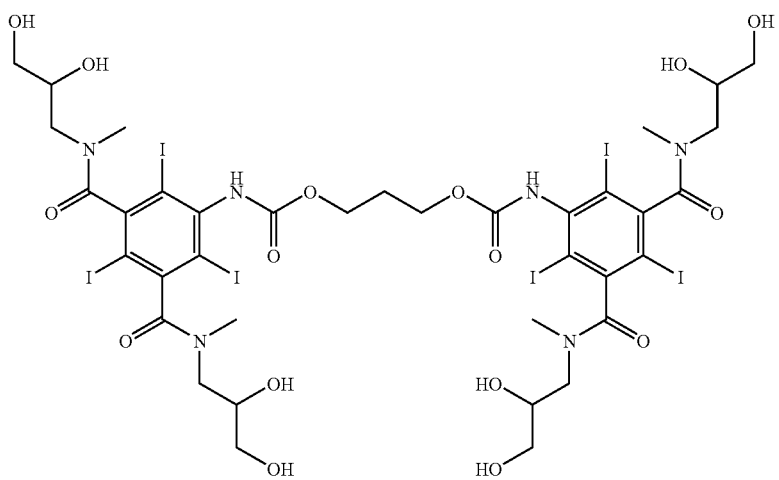 [SMILES: CN(CC(O)CO)C(=O)c1c(I)c(NC(=O)OCCCOC(=O)Nc2c(I)c(C(=O)N(C)CC(O)CO)c(I)c(C(=O)N(C)CC(O)CO)c2I)c(I)c(C(=O)N(C)CC(O)CO)c1I]

To a solution of N,N'-Diallyl-2,4,6-triiodo-5-isocyanato-N,N'-dimethyl-isophthalamide in dichloromethane was added 1,3-propane diol (0.5 equivalent). The reaction mixture was stirred for 18 hours and then purified by column chromatography to give) [3,5-Bis-(allyl-methyl-carbamoyl)-2,4,6-triiodo-phenyl]-carbamic acid 3-[3,5-bis-(allyl-methyl-carbamoyl)-2,4,6-triiodo-phenyl]carbamoyloxy-propyl ester. A

Example 14

{3-[Bis-(2,3-dihydroxy-propyl)-carbamoyl]-2,4,6-triiodo-phenyl}-carbamic acid 3,5-bis-(3-{3,5-bis-[bis-(2,3-dihydroxy-propyl)-carbamoyl]-2,4,6-triiodo-phenyl}-ureido)-2-hydroxy-propyl ester

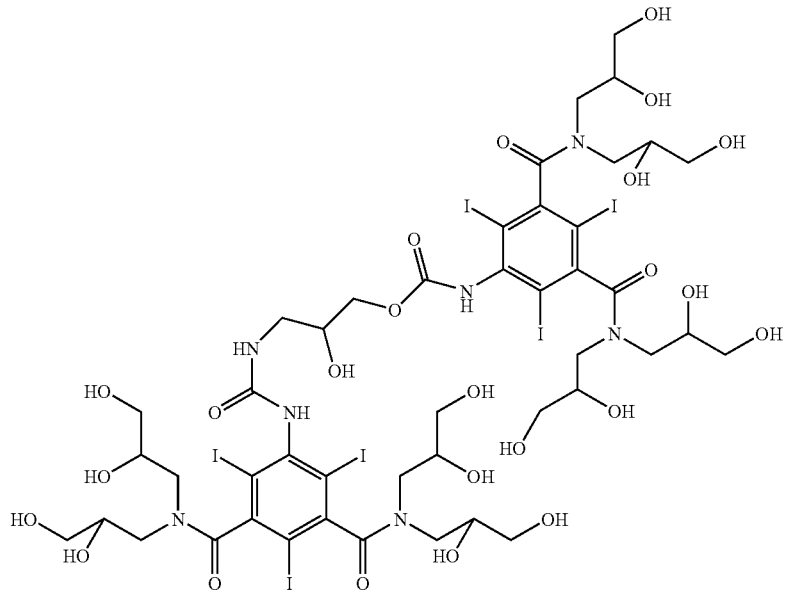 [SMILES: O=C(NCC(O)COC(=O)Nc1c(I)c(C(=O)N(CC(O)CO)CC(O)CO)c(I)c(C(=O)N(CC(O)CO)CC(O)CO)c1I)Nc1c(I)c(C(=O)N(CC(O)CO)CC(O)CO)c(I)c(C(=O)N(CC(O)CO)CC(O)CO)c1I]

To a solution of N,N'-Diallyl-2,4,6-triiodo-5-isocyanatoisophthalamide in dichloromethane was added 3-amino-1,2-propanediol (0.5 equivalent). The reaction mixture was stirred for 18 hours and then purified by column chromatography to give (3-Diallylcarbamoyl-2,4,6-triiodo-phenyl)-carbamic acid 3-{3-[3-(diallyl-propyl-carbamoyl)-5-diallylcarbamoyl-2,4,6-triiodo-phenyl]-ureido}-2-hydroxy-propyl ester. A cis-dihydroxylation using $OsO_4$ and NMMO was performed and the crude mixture was purified by preparative HPLC to give {3-[Bis-(2,3-dihydroxy-propyl)-carbarnoyl]-2,4,6-triiodo-phenyl}-carbamic acid 3,5-bis-(3-{3,5-bis-[bis-(2,3-dihydroxy-propyl)-carbarnoyl]-2,4,6-triiodo-phenyl}-ureido)-2-hydroxy-propyl ester as a white powder after freeze drying.

MS (ES$^+$, m/z): 1849.494 (100%)

The invention claimed is:

1. Compounds of formula (I)

R—Y—X—Z—R      Formula (I)

and salts or optical active isomers thereof,
wherein
X denotes a $C_2$ to $C_6$ straight of branched alkylene moiety optionally interrupted by one to two oxygen atoms or sulphur atoms and wherein the alkylene moiety optionally is substituted by one to three —OR$^1$ groups;
Y and Z independently denote urea groups or urethane groups optionally N substituted with $C_1$ to $C_4$ straight or branched alkyl groups;
R$^1$ denotes a hydrogen atom or a $C_1$ to $C_4$ straight of branched alkyl group; and
each R independently are the same or different and denote a triiodinated phenyl group.

2. Compounds as claimed in claim 1 wherein X denotes a $C_2$ to $C_5$ straight alkylene chain substituted by one or two hydroxyl groups.

3. Compounds as claimed in claim 1 where X denotes one of the groups ethylene, propylene, 2-hydroxy propylene and 2-methyl-2-hydroxy propylene.

4. Compounds as claimed in claim 1 wherein R$^1$ denotes a hydrogen atom or a methyl group.

5. Compounds as claimed in claim 1 wherein Y and Z are independently represented by urea groups of formula —N(R$^3$)—CO—N(R$^3$)— and urethane groups of formula —N(R$^3$)—CO—O— and wherein the nitrogen atom in the urethane group is linked to the moiety R; and wherein R$^3$ denotes a hydrogen atom or a $C_1$ to $C_4$ straight or branched alkyl group.

6. Compounds as claimed in claim 1 wherein each R independently are the same or different and denotes a 2,4,6-triiodinated phenyl group further substituted by two groups R$^2$ wherein each R$^2$ are the same or different and denote a hydrogen atom or a non-ionic hydrophilic moiety, provided that at least one R$^2$ group in the compound of formula (I) is a hydrophilic moiety.

7. Compounds as claimed in claim 6 wherein each R$^2$ are the same or different and denote a non-ionic hydrophilic moiety comprising esters, amides and amine moieties, optionally further substituted by a straight chain or branched chain $C_{1-10}$ alkyl groups, optionally with one or more $CH_2$ or CH moieties replaced by oxygen or nitrogen atoms and optionally substituted by one or more groups selected from oxo, hydroxyl, amino or carboxyl derivative, and oxo substituted sulphur and phosphorus atoms.

8. Compounds as claimed in claim 7 wherein each R$^2$ are the same or different and are polyhydroxy $C_{1-5}$ alkyl, hydroxyalkoxyalkyl with 1 to 5 carbon atoms or hydroxypolyalkoxyalkyl with 1 to 5 carbon atoms attached to the iodinated phenyl group via an amide linkage.

9. Compounds as claimed in claim 6 wherein each R$^2$ are the same or different and are selected from groups of the formulas

—CONH—CH$_2$—CH$_2$—OH;

—CONH—CH$_2$—CHOH—CH$_2$—OH;

—CON(CH$_3$)CH$_2$—CHOH—CH$_2$OH;

—CONH—CH—(CH$_2$—OH)$_2$;

—CON—(CH$_2$—CH$_2$—OH)$_2$;

—CON—(CH$_2$—CHOH—CH$_2$—OH)$_2$;

—CONH$_2$;

—CONHCH$_3$;

—CON(CH$_2$—CHOH—CH$_2$—OH)(CH$_2$—CH$_2$—OH);

—CONH—C(CH$_2$—OH)$_3$;

—CONH—CH(CH$_2$—OH)(CHOH—CH$_2$—OH);

—CONH—CH(CH$_2$—OH)(CHOH—CH$_2$—OH); and

-morpholine-4-carbonyl.

10. Compounds as claimed in claim 9 wherein each R$^2$ are the same or different and are selected from groups of the formulas —CONH—CH$_2$—CHOH—CH$_2$—OH and —CON—(CH$_2$—CHOH—CH$_2$—OH)$_2$.

11. Compounds as claimed in claim 5 and of formulas (IIa), (IIb) and (IIc)

R—NH—CO—N(R$^3$)—X—N(R$^3$)—CO—NH—R  (IIa)

R—NH—CO—O—X—O—CO—NH—R  (IIb)

R—NH—CO—O—X—N(R$^3$)—CO—NH—R  (IIc)

wherein:
each R independently are the same or different and denotes a 2,4,6-triiodinated phenyl group further substituted by two groups R$^2$ wherein each R$^2$ are the same or different and denote a hydrogen atom or a non-ionic hydrophilic moiety, provided that at least one R$^2$ group in the compound of formula (I) is a hydrophilic moiety;

X denotes a C$_2$ to C$_6$ straight of branched alkylene moiety optionally interrupted by one to two oxygen atoms or sulphur atoms and wherein the alkylene moiety optionally is substituted by one to three —OR$^1$ groups; and R$^3$ denotes a hydrogen atom or a C$_1$ to C$_4$ straight or branched alkyl group.

12. Compounds as claimed in claim 11 wherein each group R are the same, all R$^2$ groups denote non-ionic hydrophilic moieties linked to the iodinated phenyl moiety by amide groups and X denotes straight chain alkylene groups with 2 to 5 carbon atoms, or straight or branched mono-hydroxylated alkylene groups where the hydroxyl substituent are at positions that are not adjacent to nitrogen functions.

13. Compounds as claimed in claim 1 selected from the group consisting of:

1,3-bis-[N,N'-Bis-(2,3-dihydroxy-propyl)-2,4,6-triiodo-5-ureido-isophthalamide]-2-hydroxypropane;

1,3-bis-[N,N'-Bis-(2,3-dihydroxy-propyl)-2,4,6-triiodo-5-(methly-ureido)-isophthalamide]-ethylene;

1,3-bis-[N,N'-Bis-(4-morpholine)-2,4,6-triiodo-5-ureido-isophthalamide]-2-hydroxypropane;

1,3-Bis-[bis-N,N'-methyl-N,N'-bis-(2,3-dihydroxy-propyl)-2,4,6-triiodo-5-ureido-isophthalamide]-2-hydroxypropane;

1,3-bis-(N,N,N',N'-tetrakis-(2,3-dihydroxypropyl))-2,4,6-triiodo-5-ureido-isophthalamide]-2-hydroxypropane;

1,3-bis-[N,N'-Bis-(2,3-dihydroxy-propyl)-2,4,6-triiodo-5-carbamido-isophthalamide]-2-methyl-2-hydroxymethylpropane;

{3,5-Bis-[bis-(2,3-dihydroxy-propyl)-carbamoyl]-2,4,6-triiodo-phenyl}-carbamic acid 2-{3,5-bis-[bis-(2,3-dihydroxy-propyl)-carbamoyl]-2,4,6-triiodo-phenylcarbamoyloxy}-ethyl ester;

{3,5-Bis-[bis-(2,3-dihydroxy-propyl)-carbamoyl]-2,4,6-triiodo-phenyl}-carbamic acid 3,5-bis-{3-[bis-(2,3-dihydroxy-propyl)-carbamoyl]-2,4,6-triiodo-phenylcarbamoyloxy}-propyl ester;

[3,5-Bis-(2,3-dihydroxy-propylcarbamoyl)-2,4,6-triiodo-phenyl]-carbamic acid 2-[3,5-bis-(2,3-dihydroxy-propylcarbamoyl)-2,4,6-triiodo-phenylcarbamoyloxy]-ethyl ester;

[3,5-Bis-(2,3-dihydroxy-propylcarbamoyl)-2,4,6-triiodo-phenyl]-carbamic acid 3-[3,5-Bis-(2,3-dihydroxy-propylcarbamoyl)-2,4,6-triiodo-phenylcarbamoyloxy]-propyl ester;

[3,5-Bis-(2,3-dihydroxy-propylcarbamoyl)-2,4,6-triiodo-phenyl]-carbamic acid 3-[3,5-Bis-(2,3-dihydroxy-propylcarbamoyl)-2,4,6-triiodo-phenylcarbamoyloxy]-2-hydroxy-propyl ester;

[3,5-Bis-(2,3-dihydroxy-propylcarbamoyl)-2,4,6-triiodo-phenyl]-carbamic acid 3-[3,5-Bis-(2,3-dihydroxy-propylcarbamoyl)-2,4,6-triiodo-phenylcarbamoyloxy]-2-hydroxymethyl-propyl ester;

{3,5-Bis-[bis-(2,3-dihydroxy-propyl)-carbamoyl]-2,4,6-triiodo-phenyl}-carbamic acid 3-{3,5-Bis-[bis-(2,3-dihydroxy-propyl)-carbamoyl]-2,4,6-triiodo-phenylcarbamoyloxy}propyl ester; and {3-[Bis-(2,3-dihydroxy-propyl)-carbamoyl]-2,4,6-triiodo-phenyl}-carbamic acid 3,5-bis-(3-{3,5-bis-[bis-(2,3-dihydroxy-propyl)-carbamoyl]-2,4,6-triiodo-phenyl}-ureido)-2-hydroxy-propyl ester.

14. An X-ray diagnostic composition comprising a compound of formula (I) as defined in claim 1 together with a pharmaceutically acceptable carriers or excipient.

15. A method of imaging comprising administration of compounds of formula (I) as defined in claim 1 to the human or animal body, examining the body with a diagnostic device and compiling data from the examination and optionally analysing the data.

\* \* \* \* \*